United States Patent [19]

Morris, Jr.

[11] 4,158,674

[45] Jun. 19, 1979

[54] PROCESS FOR DISPLACING NUCLEAR IODINE FROM SUBSTITUTED BENZENES WITH CHLORINE

[75] Inventor: Earl D. Morris, Jr., Midland, Mich.

[73] Assignee: The Dow Chemical Company, Midland, Mich.

[21] Appl. No.: 939,508

[22] Filed: Sep. 5, 1978

[51] Int. Cl.$^2$ .............................................. C07C 25/00
[52] U.S. Cl. ................................................ 260/650 R
[58] Field of Search .................................... 260/650 R

[56] References Cited

U.S. PATENT DOCUMENTS 3,577,471   5/1971   McNulty et al. ................ 260/650 R Primary Examiner—Delbert E. Gantz
Assistant Examiner—Joseph A. Boska
Attorney, Agent, or Firm—Michael L. Glenn

[57] ABSTRACT

In a halobenzene mixture containing benzenes bearing nuclear iodine substituents, the iodine is displaced by chlorine by introducing gaseous chlorine into the mixture at a temperature of from about 100° C. to about 250° C. The displacement of iodine produces chlorobenzenes, which can then be separated from the liberated iodine by conventional methods such as distillation.

5 Claims, No Drawings

4,158,674

PROCESS FOR DISPLACING NUCLEAR IODINE FROM SUBSTITUTED BENZENES WITH CHLORINE

BACKGROUND OF THE INVENTION

This invention relates to the displacement of nuclear iodine substituents from an iodobenzene with gaseous chlorine.

The prior art teaches that the treatment of benzene bearing nuclear iodine substituents with gaseous (molecular) chlorine does not displace the iodine substituents. See, e.g., J. Am. Chem. Soc., 79:4187–4191 (1957); Huyser, Methods in Free Radical Chemistry, p. 134, Marcel Dekker (1969). Milligan et al., J. Am. Chem. Soc., 84:158–162 (1962), teach that iodine substituents are displaced by certain more active chlorinating agents, such as iodine monochloride, in an irradiated system. However, the prior art is deficient in that it fails to identify an economical manner in which chlorinating agents can be used to displace nuclear iodine substituents in iodobenzene mixtures.

It is particularly desirable in the preparation of chlorobenzenes from chlorine and benzene or monochlorobenzene that a method is identified to displace nuclear iodine substituents which result from the presence of iodine in the chlorine feed or from other sources.

SUMMARY OF THE INVENTION

This invention is a method for displacing with chlorine moieties nuclear iodine substituents from an iodobenzene compound which comprises introducing gaseous chlorine into the iodobenzene at a temperature of from about 100° to about 250° C., so as to displace one or more iodine substituents and produce chlorobenzene compounds. The chlorobenzene is then separated from the displaced iodine.

Surprisingly, the practice of the instant process replaces nuclear iodine substituents with chlorine. This replacement improves the purity of chlorobenzenes where corresponding benzene compounds are present having iodine in place of at least one chlorine substituent.

DETAILED DESCRIPTION OF THE INVENTION

The iodobenzene is a compound comprising a phenyl moiety which bears at least one iodine substituent attached to a carbon atom in the aromatic ring and other substituents which do not substantially hinder the displacement of iodine with chlorine. It is desirable that the phenyl moiety bear only one iodine substituent. The preferred nuclear substituents in addition to the iodine moiety include chlorine, bromine and hydrogen. Some of these other nuclear substituents, in particular bromine, will also exchange with chlorine.

The iodobenzene can be a single compound or a mixture of suitable compounds. The iodobenzene can also be present in a mixture with other compounds not bearing iodine substituents exchangeable with chlorine, such as chlorobenzenes. Especially preferred iodobenzenes are those comprising a phenyl moiety which bears one iodine substituent, at least one chlorine substituent and a remaining number of hydrogen substituents on the carbon atoms of the aromatic ring. These especially preferred iodobenzenes include dichloroiodobenzene, chloroiodobenzene, trichloroiodobenzene, and the like.

The iodobenzene should be present in the liquid phase when the gaseous chlorine is introduced. The chlorine can conveniently be sparged through or otherwise placed in intimate contact with the iodobenzene medium. Agitation of the medium during addition of the chlorine is desirable.

The chlorine can be continuously or batchwise introduced into the medium during the replacement reaction. If the iodobenzene is present as a minor impurity in a chlorobenzene medium, the chlorine is conveniently introduced continuously during the initial phases of the reaction and the addition is terminated after several minutes when the medium is substantially saturated with chlorine. The displacement reaction continues for several minutes after the addition of chlorine is terminated. The total amount of chlorine introduced into the medium is advantageously a large molar excess relative to the iodine to be replaced.

The rapidity of replacement of iodine with chlorine is dependent on the temperature during contact, the particular iodobenzene involved, and numerous other factors. Desirably, the temperature of the medium during the replacement reaction is at least about 100° C., preferably at least about 150° C., to promote rapid reaction. Lower temperatures are operable as long as the iodobenzene is present in liquid reaction medium, but generally result in an uneconomically slow rate of reaction. The maximum reaction temperature is limited by the temperature at which substantial thermal degradation of reactants or products occurs and the temperature at which the vapor pressure of reactants and products becomes inconveniently large. Typically, the temperature of the medium during the replacement reaction is preferably no greater than about 250° C., more preferably no greater than about 200° C.

The pressure during the replacement reaction is not critical. Conveniently, atmospheric pressure is employed. However, it can be advantageous to employ superatmospheric pressures to maintain the iodobenzene and chlorobenzene in the liquid phase during the reaction.

The presence of iron in contact with the medium facilitates the addition of liberated iodine to the aromatic nucleus. Therefore, it is desirable to utilize a reaction vessel having some material other than iron in contact with the medium. It is also desirable to remove iron-derived chlorination catalysts, such as ferric chloride or finely divided iron, from the reaction medium prior to the replacement reaction. Iron-derived catalysts can be conveniently removed by conventional methods, such as flash distillation of the medium prior to introducing chlorine for the replacement reaction.

The replacement of iodine with chlorine by the practice of the instant method does not require irradiation of the medium to proceed. However, it is operable and convenient to expose the medium to visible light and to carry out the reaction in a vessel having a transparent region through which the medium can be observed. The progression of the reaction can then be gauged by a color change in the medium to a red or orange color indicating the presence of free iodine released in the replacement reaction.

After the iodine has been released, the iodine can be separated from the chlorobenzene in any convenient manner. Typically, the iodine can be readily removed from the chlorobenzene by distillation of the mixture. Advantageously, the replacement reaction with chlorine and the subsequent separation step can be repeated with the distilled predominantly chlorobenzene product to remove residual iodine.

The specific examples that follow illustrate the invention, but are not to be taken as limiting its scope.

EXAMPLE 1

A mixture of polychlorobenzenes, produced in the chlorination of benzene or monochlorobenzene to more highly chlorinated derivatives by conventional methods, is flash distilled in a glass reactor at a temperature of about 250° C. to remove ferric chloride. These polychlorobenzenes consist predominantly of a mixture of 1,2,4-trichlorobenzene, 1,2,3,4- and 1,2,4,5-tetrachlorobenzene, pentachlorobenzene and analogs of the aforementioned polychlorobenzenes where an iodine substituent has replaced one or more of the chlorines. Calcium oxide is added to the polychlorobenzenes before flash distillation to further reduce the ferric chloride present.

Eight hundred grams of the flash distilled polychlorobenzenes containing 250 parts per million by weight (ppm) of iodine as determined by conventional methods are transferred to a second glass reaction vessel. The polychlorobenzenes are heated to and maintained at a temperature of from 150° C. to 200° C. Gaseous chlorine is bubbled slowly (about 200 cubic centimeters per minute) into the heated polychlorobenzenes for about 5 minutes. The introduction of chlorine is then terminated. The mixture is held at the reaction temperature for at least 15 minutes, during which time the color of the mixture turns red.

The polychlorobenzene mixture is then heated to boiling and the distillate removed overhead through a ten-plate distillation column. The first portion of the distillate is a very deep red in color. The distillation is continued until fresh portions of distillate are clear.

The polychlorobenzene is then cooled to a temperature of from 150° C. to 200° C. and the aforementioned chlorine introduction, reaction period and subsequent distillation are repeated. The polychlorobenzene left after the removal of a total of about 25 milliliters of distillate in the two distillations is determined by conventional analytical techniques to contain only 2 ppm of iodine.

EXAMPLE 2

One gram of 1,2-dichloro-4-iodobenzene is added to 935 grams of 1,2,4-trichlorobenzene. This mixture is determined by conventional analytical techniques to contain 271 ppm iodine. In the manner set out in Example 1, the mixture is heated to 150° C. and gaseous chlorine is introduced for 5 minutes. The temperature of the mixture is elevated to 200° C. and after about 15 minutes a dark red color is exhibited. Fifteen grams of deep red distillate is removed in a first distillation. The chlorination of the undistilled material is repeated and 10 grams of an orange distillate is removed in a second distillation.

The polychlorobenzene left after the second distillation is found by conventional analytical techniques to contain only 0.8 ppm of iodine.

EXAMPLE 3

One gram of 1-chloro-4-iodobenzene is mixed with 905 grams of 1,2,4-trichlorobenzene. This mixture is found by conventional analytical techniques to contain 358 ppm iodine. The mixture is twice chlorinated and distilled in the manner set out in Example 2. A total of 42 grams of distillate is removed in the two distillations.

The polychlorobenzene left after the second distillation is found by conventional analytical techniques to contain only 2 ppm iodine.

What is claimed is:

1. A process for replacing nuclear iodine substituents from an iodobenzene compound with chlorine moieties comprising:
    (a) introducing gaseous chlorine into the iodobenzene compound at a temperature of from about 100° C. to about 250° C. in absence of an activating amount of irradiation, so as to displace one or more iodine substituents and thereby produce a chlorobenzene compound; and
    (b) separating the chlorobenzene compound from the displaced iodine.

2. The process as defined in claim 1 further comprising the step of substantially completely removing iron or ferric chloride compounds from contact with the iodobenzene prior to introducing the chlorine.

3. The process as defined in claim 2 wherein the iodobenzene compound is selected from the group consisting of chloroiodobenzene, dichloroiodobenzene, trichloroiodobenzene and tetrachloroiodobenzene.

4. The process as defined in claim 3 wherein the temperature during introduction of gaseous chlorine is from about 150° C. to about 200° C.

5. The process as defined in claim 4 wherein the chlorobenzene compound is separated from the iodine by distillation.

* * * * *